United States Patent
Uehara et al.

(10) Patent No.: US 7,279,589 B2
(45) Date of Patent: Oct. 9, 2007

(54) PREPARATION OF 1-(ALKOXYSILYL)ETHYL-1,1,3,3-TETRA-METHYLDISILOXANE

(75) Inventors: Katsuhiro Uehara, Joetsu (JP); Tohru Kubota, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 11/502,533

(22) Filed: Aug. 11, 2006

(65) Prior Publication Data

US 2007/0037997 A1   Feb. 15, 2007

(30) Foreign Application Priority Data

Aug. 15, 2005   (JP)   ............... 2005-235246

(51) Int. Cl.
  *C07F 7/08* (2006.01)
(52) U.S. Cl. .................................... 556/467
(58) Field of Classification Search .............. None
  See application file for complete search history.

(56) References Cited

U.S. PATENT DOCUMENTS

| 4,772,675 A | 9/1988 | Klosowski et al. |
| 4,808,664 A | 2/1989 | Saam |
| 4,871,827 A | 10/1989 | Klosowski et al. |
| 4,888,404 A | 12/1989 | Klosowski et al. |
| 5,051,455 A | 9/1991 | Chu et al. |
| 5,276,123 A | 1/1994 | King et al. |
| 5,403,881 A | 4/1995 | Okawa et al. |
| 2003/0120016 A1 | 6/2003 | Okawa et al. |

FOREIGN PATENT DOCUMENTS

| JP | 62-207383 A | 9/1987 |
| JP | 1-197509 A | 8/1989 |
| JP | 6-166810 A | 6/1994 |
| JP | 6-172536 A | 6/1994 |
| JP | 07-70551 A | 3/1995 |
| JP | 09-012709 A | 1/1997 |
| JP | 09-309889 A | 12/1997 |
| JP | 2000-256374 A | 9/2000 |
| JP | 2001-348429 A | 12/2001 |

OTHER PUBLICATIONS

J. V. Crivello et al. Journal of Polymer Science, Part A: Polymer Chemistry, vol. 31, 3121-32 (1993).

*Primary Examiner*—Samuel Barts
(74) *Attorney, Agent, or Firm*—Westerman, Hattori, Daniels & Adrian, LLP.

(57) ABSTRACT

A 1-(alkoxysilyl)ethyl-1,1,3,3-tetramethyldisiloxane is prepared by adding a vinyl-containing alkoxysilane in portions to 1,1,3,3-tetramethyldisiloxane in the presence of a rhodium compound, and effecting reaction.

19 Claims, No Drawings

US 7,279,589 B2

PREPARATION OF 1-(ALKOXYSILYL)ETHYL-1,1,3,3-TETRA-METHYLDISILOXANE

CROSS-REFERENCE TO RELATED APPLICATION

This non-provisional application claims priority under 35 U.S.C. §119(a) on Patent Application No. 2005-235246 filed in Japan on Aug. 15, 2005, the entire contents of which are hereby incorporated by reference.

TECHNICAL FIELD

This invention relates to a method for preparing 1-(alkoxysilyl)ethyl-1,1,3,3-tetramethyldisiloxanes in high yields and at high selectivity, which are useful in many industrial fields, for example, as surface treating agents for inorganic powder, modifiers for silicone fluids or the like, starting materials for silicone sealants, silane coupling agents or the like, and intermediates in various synthesis processes.

BACKGROUND ART

For the preparation of 1-(alkoxysilyl)ethyl-1,1,3,3-tetramethyldisiloxanes, several means are known in the art, but suffer from problems. For example, U.S. Pat. No. 4,871,827 (JP-A 62-207383), U.S. Pat. No. 4,772,675, JP-A 1-197509, U.S. Pat. No. 5,276,123 (JP-A 6-172536), JP-A 6-166810, JP-A 7-70551, JP-A 9-12709, JP-A 9-309889, JP-A 2000-256374, and JP-A 2001-348429 disclose methods for preparing 1-(alkoxysilyl)ethyl-1,1,3,3-tetramethyldisiloxanes by reacting vinyl-containing alkoxysilanes with 1,1,3,3-tetramethyldisiloxane under varying conditions and in the presence of platinum compounds as the reaction catalyst. More specifically, in U.S. Pat. No. 4,871,827 to Klosowski et al., a reactor is charged with vinyltrimethoxysilane (which is a vinyl-containing alkoxysilane), 1,1,3,3-tetramethyldisiloxane in a 2-times molar amount relative to moles of vinyltrimethoxysilane, and a platinum catalyst all in their entirety, whereupon reaction is effected to form 1-(trimethoxysilyl)ethyl-1,1,3,3-tetramethyldisiloxane (which is a 1-(alkoxysilyl)ethyl-1,1,3,3-tetramethyldisiloxane). It is noted that for the synthesis of 1-(alkoxysilyl)ethyl-1,1,3,3-tetramethyl-disiloxane, the theoretically necessary amount of 1,1,3,3-tetramethyldisiloxane is an equimolar amount relative to a molar amount of the vinyl-containing alkoxysilane. However, since 1,1,3,3-tetramethyldisiloxane has a chemical structure that possesses per molecular two sites (H—Si groups) capable of addition reaction with vinyl groups, there is a likelihood that a by-product forms in which the vinyl-containing alkoxysilane adds at both the sites. To alleviate this problem, Klosowski patent recommends to use a large excess of 1,1,3,3-tetramethyldisiloxane, which is as large as 2 to 4 times the molar amount of the vinyl-containing alkoxysilane. Smaller amounts of 1 to 2 times molarity are unsatisfactory because more by-product is formed, resulting in a substantial drop of yield.

However, even the mixing conditions recommended by Klosowski patent are still insufficient because the percent yield is very low. For instance, in the example of Klosowski patent where reaction is performed using vinyltrimethoxysilane and 1,1,3,3-tetramethyldisiloxane in a molar ratio of 1/2, the yield of 1-(trimethoxysilyl)ethyl-1,1,3,3-tetramethyldisiloxane is about 80% relative to the vinyltrimethoxysilane and merely about 40% relative to the 1,1,3,3-tetramethyldisiloxane. The means of using a large molar excess of 1,1,3,3-tetramethyldisiloxane relative to the vinyl-containing alkoxysilane manifests an economical disadvantage because the cost of 1,1,3,3-tetramethyl-disiloxane becomes increased and the percent yield per unit volume is inevitably low. For the preparation of 1-(alkoxysilyl)ethyl-1,1,3,3-tetramethyldisiloxanes, it would then be desirable to select a set of reaction conditions that eliminates a need for a large molar excess of 1,1,3,3-tetramethyldisiloxane relative to the vinyl-containing alkoxysilane and achieves higher yields than in the prior art methods.

Under the circumstances, Crivello et al., Journal of Polymer Science, Part A: Polymer Chemistry, Vol. 31, 3121-32 (1993), report that when equimolar amounts of a vinyl-containing alkoxysilane (e.g., vinyltrimethoxysilane) and 1,1,3,3-tetramethyldisiloxane are reacted in the presence of $RhCl(PPh_3)_3$ as a reaction catalyst, a 1-(alkoxysilyl)-ethyl-1,1,3,3-tetramethyldisiloxane is prepared in higher yields than the process conducted in the presence of platinum catalysts. Specifically, a reactor is charged with $RhCl(PPh_3)_3$ on a polymer carrier, and equimolar amounts of 1,1,3,3-tetramethyldisiloxane and vinyltrimethoxysilane, and toluene all in their entirety, whereupon the contents are heated at 80° C. and reacted for 16 hours. The toluene and excessive reactants are removed from the reaction mixture, which is then distilled, collecting 1-(trimethoxysilyl)ethyl-1,1,3,3-tetramethyldisiloxane in a yield of 85.6%. Although this method advantageously eliminates the need for a large molar excess of 1,1,3,3-tetramethyldisiloxane relative to the vinyl-containing alkoxysilane, the yield of 1-(alkoxysilyl)-ethyl-1,1,3,3-tetramethyldisiloxane is still insufficient. There still exists a need for a method capable of offering higher yields.

It is described in the report of Crivello that the 1-(trimethoxysilyl)ethyl-1,1,3,3-tetramethyldisiloxane product is a mixture of two isomers resulting from addition of H—Si groups to a $CH_2$=CH—Si group, that is, a compound having a —$Si(CH_2)_2Si$— linkage, i.e., 1-[2-(trimethoxysilyl)-ethyl]-1,1,3,3-tetramethyldisiloxane (referred to as beta-adduct) and a compound having a —$SiCH(CH_3)Si$— linkage, i.e., 1-[1-(trimethoxysilyl)ethyl]-1,1,3,3-tetramethyl-disiloxane (referred to as alpha-adduct), and that the ratio of isomers, i.e., alpha-adduct/beta-adduct ratio is 1/2 (=33/67). As to the reaction in the presence of platinum catalysts, it is described in U.S. Pat. No. 5,276,123 that the 1-(trimethoxysilyl)ethyl-1,1,3,3-tetramethyldisiloxane product contains not only a compound having a —$Si(CH_2)_2Si$—linkage, i.e., 1-[2-(trimethoxysilyl)ethyl]-1,1,3,3-tetramethyldisiloxane (beta-adduct), but also an isomeric compound having a —$SiCH(CH_3)Si$— linkage, i.e., 1-[1-(trimethoxysilyl)ethyl]-1,1,3,3-tetramethyldisiloxane (alpha-adduct) and that the product is a mixture of isomers in an alpha-adduct/beta-adduct ratio of 1/2 (=33/67).

It is known that the hydrolysis rate of an alkoxysilyl group becomes slower as the alkyl substituent bonded to the alkoxysilyl group is bulkier so that more steric hindrance is provided during reaction. Then, as compared with the beta-adduct having primary carbon bonded to its alkoxysilyl group, the alpha-adduct having secondary carbon bonded has a low hydrolysis rate. Since higher hydrolysis rates are preferred in the area of application where the relevant compounds are used, there exists a need for a method capable of affording a less amount of alpha-adduct isomer, namely a high selectivity.

DISCLOSURE OF THE INVENTION

Accordingly, an object of the present invention is to provide a method for preparing a 1-(alkoxysilyl)ethyl-1,1,3,3-tetramethyldisiloxane in high yields and at a high selectivity.

The present invention provides a method for preparing a 1-(alkoxysilyl)ethyl-1,1,3,3-tetramethyldisiloxane having the general formula (2), the method comprising adding a vinyl-containing alkoxysilane having the general formula (1) to 1,1,3,3-tetramethyldisiloxane in the presence of a rhodium compound, and effecting reaction.

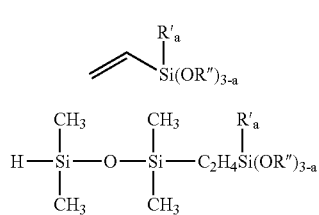

Herein R' and R" are methyl or ethyl and may be the same or different, and a is equal to 0, 1 or 2.

BENEFITS OF THE INVENTION

The method of the invention is successful in preparing 1-(alkoxysilyl)ethyl-1,1,3,3-tetramethyldisiloxane products having formula (2) in high yields and at a high selectivity. Since the 1-(alkoxysilyl)ethyl-1,1,3,3-tetramethyldisiloxanes as prepared by the inventive method have a Si—H bond at one end of a siloxane chain and an alkoxysilyl group at the other end, they undergo addition reaction with various compounds and polymers having olefinic organic groups (e.g., vinyl and allyl groups) in the presence of platinum catalysts, to chemically bond therewith, thereby incorporating therein a siloxane structure having (alkoxysilyl)ethyl group. Since the alkoxysilyl group has a chemical bond function of forming a siloxane bond with a surface of inorganic substances such as glass and metals through hydrolytic condensation reaction and a function of forming crosslinks between main chains of a polymer modified therewith, the inventive products are useful as surface treating agents for inorganic powder, modifiers for silicone fluids or the like, starting materials for silicone sealants, silane coupling agents or the like. They are also useful as intermediates in various synthesis processes.

DESCRIPTION OF THE PREFERRED EMBODIMENTS

The method of the invention starts with two reactants. One reactant, 1,1,3,3-tetramethyldisiloxane is a well-known compound and available in large quantities on a commercial scale.

The other reactant is any of vinyl-containing alkoxysilane compounds having the general formula (1):

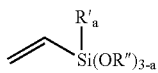

wherein R' and R" are methyl or ethyl and may be the same or different, and a is equal to 0, 1 or 2. They are also well-known compounds and can be prepared by any well-known techniques. They are available in a large amount and a low cost with an industrial scale. Because of low cost and mass availability on a commercial scale, those compounds of formula (1) wherein R' is methyl, R" is methyl or ethyl and a is 0 or 1 are preferred. Examples of the compounds of formula (1) include, but are not limited to, the structures shown below.

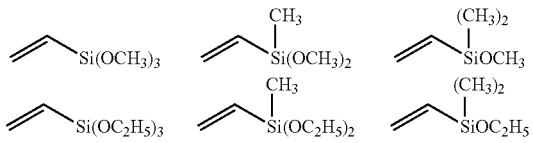

In the practice of the invention, the molar ratio of vinyl-containing alkoxysilane compound having formula (1) to 1,1,3,3-tetramethyldisiloxane is preferably in a range from 0.8 to 1.2, more preferably from 0.9 to 1.1. If this molar ratio is less than 0.8, that is, if 1,1,3,3-tetramethyl-disiloxane is present in excess, more of 1,1,3,3-tetramethyl-disiloxane is left unreacted, leading to an economical disadvantage. If the molar ratio is more than 1.2, that is, if the vinyl-containing alkoxysilane is present in excess, there is a likelihood that one more molecule of the vinyl-containing alkoxysilane having formula (1) adds to the resultant 1-(alkoxysilyl)ethyl-1,1,3,3-tetramethyldisiloxanes having formula (2), forming a by-product having the following general formula (3):

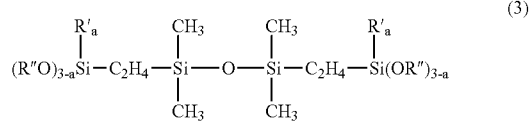

wherein R', R" and a are as defined above, which is sometimes referred to as "bis-adduct." This likelihood tends to reduce the percent yield.

The reaction catalyst used herein is a rhodium compound. A choice may be made among various rhodium compounds as the reaction catalyst. In order for stable addition reaction to proceed to completion, especially at a reaction temperature of less than 60° C., it is preferred that rhodium compounds do not contain as a ligand a phosphorus-containing compound which can interfere with addition reaction between H—Si groups and vinyl groups. Rhodium compounds which contain rhodium halides or 1,5-cyclooctadiene as a ligand are more preferred. Illustrative, non-limiting examples of suitable rhodium compounds are given below.

RhCl$_3$.xH$_2$O
RhCl$_3$
RhBr$_3$.2H$_2$O
RhBr$_3$
RhI$_3$
Rh$_6$(CO)$_{16}$
Rh$_4$(CO)$_{12}$
[RhCl(CO)$_2$]$_2$
Rh(acac)$_3$
[Rh(acac)$_2$]$_2$
Rh(acac)(CO)$_2$
(NH$_4$)$_3$[RhCl$_6$].xH$_2$O
[Rh(NH$_3$)$_5$Cl]Cl$_2$
[Rh(C$_7$H$_{15}$COO)$_2$]$_2$
[Rh(CF$_3$COO)$_2$]$_2$
[Rh(C$_2$H$_4$)$_2$(acac)]
[Rh(C$_2$H$_4$)$_2$]$_2$
[RhCl(C$_8$H$_{14}$)$_2$]$_2$
[RhCl(C$_7$H$_8$)]$_2$
(CH$_3$)$_5$C$_5$Rh(CO)$_2$

[(CH$_3$)$_5$C$_5$RhCl$_2$]$_2$
Rh(C$_2$H$_8$N$_2$)$_3$Cl$_3$·3H$_2$O
[RhCl(cod)]$_2$
[RhOH(cod)]$_2$
[Rh(cod)$_2$(acac)]
[Rh(cod)(acac)]
Rh(cod)$_2$BF$_4$
Rh(cod)$_2$SO$_3$CF$_3$
RhCl(PPh$_3$)$_3$
[Rh(acac)(CO)(PPh$_3$)$_3$]
trans-[RhH(CO)(PPh$_3$)$_3$]

As used herein, the abbreviation "acac" designates acetylacetonato, "cod" 1,5-cyclooctadiene, and "PPh$_3$" triphenylphosphine.

The rhodium compound is used in such amounts that $0.1 \times 10^{-6}$ to 0.1 mole, especially $1 \times 10^{-6}$ to 0.01 mole of Rh atom is present per mole of 1,1,3,3-tetramethyldisiloxane. Less than $0.1 \times 10^{-6}$ mole of Rh atom may achieve less catalysis whereas more than 0.1 mole of Rh atom may be uneconomical.

The method of the invention is characterized in that the vinyl-containing alkoxysilane is added to 1,1,3,3-tetramethyldisiloxane in the presence of the rhodium compound. Prior to the addition of the vinyl-containing alkoxysilane, the rhodium compound is premixed with 1,1,3,3-tetramethyldisiloxane. This premix is generally obtained by mixing powder rhodium compound with liquid 1,1,3,3-tetramethyldisiloxane. Alternatively, for the purpose of facilitating handling during the process or improving the catalytic activity upon reaction initiation, powder rhodium compound may be previously dissolved in an organic solvent or a mixture of an organic solvent and a small amount of 1,1,3,3-tetramethyldisiloxane, and the resulting catalyst solution may then be mixed with previously charged 1,1,3,3-tetramethyldisiloxane.

Examples of the organic solvent used herein include aromatic hydrocarbons such as toluene, xylene, ethylbenzene, mesitylene, decalin, and tetralin; aliphatic hydrocarbons such as hexane, isooctane, octane, decane, undecane, dodecane, tetradecane, hexadecane, and paraffin; aprotic polar solvents such as tetrahydrofuran, acetonitrile and cyclohexanone; and vinyl-containing siloxanes such as divinyltetramethyldisiloxane.

In the process of the present invention, it is necessary to add the vinyl-containing alkoxysilane to 1,1,3,3-tetramethyldisiloxane.

If the charges of 1,1,3,3-tetramethyldisiloxane and vinyl-containing alkoxysilane are reacted all at once, even in the presence of a rhodium compound, undesired results are obtained including reduced percent yields due to a phenomenon that reactivity lowers or more by-products form and an increased isomeric ratio of alpha-adduct/beta-adduct (more alpha-adduct formation). If 1,1,3,3-tetramethyldisiloxane is added to the vinyl-containing alkoxysilane compound to react them, undesired results would occur that the by-product (bis-adduct) of the above-said general formula (3) would occur in a large amount.

The reaction temperature is preferably in the range from 0° C. to 150° C., more preferably from 0° C. to less than 60° C. At temperatures below 0° C., the reaction rate becomes slow, requiring a time until the completion of reaction, against economy. At temperatures above 150° C., more by-products may form to lower the percent yield and the isomeric ratio of alpha-adduct/beta-adduct may increase (more alpha-adduct forms). It is understood that at a reaction temperature in the range from 0° C. to less than 60° C., better results are obtained, for example, the amount of by-product formed decreases to further improve the percent yield, and the isomeric ratio of alpha-adduct/beta-adduct decreases (less alpha-adduct forms).

It is noted that the 1-(alkoxysilyl)ethyl-1,1,3,3-tetramethyldisiloxane of formula (2) includes two isomers, alpha-adduct and beta-adduct. The alpha- and beta-adducts have structures of the general formulae (4) and (5), respectively.

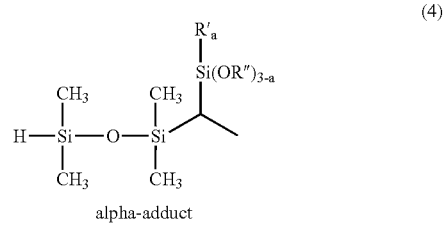

(4)

alpha-adduct

Herein R', R" and a are as defined above.

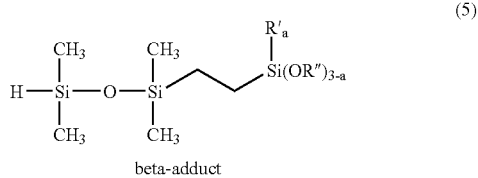

(5)

beta-adduct

Herein R', R" and a are as defined above.

In the preparation method of the invention, the amount of alpha-adduct is significantly reduced as compared with the prior art methods, and beta-adduct is obtained at a high selectivity, with the isomeric ratio of alpha-adduct/beta-adduct being (25 or less)/(75 or more). When a reaction temperature is selected within the range from 0° C. to less than 60° C., the amount of alpha-adduct is further reduced, beta-adduct is obtained at a higher selectivity, with the isomeric ratio of alpha-adduct/beta-adduct being (20 or less)/(80 or more).

Although a reaction solvent is not essentially necessary in the practice of the invention, it may be used if necessary for improving the homogeneity of the reaction system, increasing the volume of the reaction system for more efficient agitation, or controlling the temperature of the reaction system. Examples of the solvent used herein include aromatic hydrocarbons such as toluene, xylene, ethylbenzene, mesitylene, decalin, and tetralin; aliphatic hydrocarbons such as hexane, isooctane, octane, decane, undecane, dodecane, tetradecane, hexadecane, and paraffin; aprotic polar solvents such as tetrahydrofuran, acetonitrile and cyclohexanone; and siloxanes such as hexamethyldisiloxane, alone or in admixture. The solvent may be mixed together in premixing 1,1,3,3-tetramethyldisiloxane with the rhodium compound, or it may be mixed with the vinyl-containing alkoxysilane to form a solution which is added dropwise to the premix of 1,1,3,3-tetramethyldisiloxane and the rhodium compound.

In the practice of the invention, the reaction may be effected under atmospheric pressure or increased pressure. In general, atmospheric pressure is sufficient, although the pressure is not particularly limited.

With respect to the atmosphere of the reaction system where the inventive method is implemented, the presence of water is essentially undesired because compounds containing hydrolyzable alkoxysilyl groups are handled. An inert gas atmosphere which is substantially free of moisture is preferred. The reaction system favors an inert gas atmosphere from the standpoint of fire prevention as well because flammable compounds are handled. Examples of the inert gas are nitrogen, argon and the like.

In the inventive method, the reaction time for adding the vinyl-containing alkoxysilane compound to 1,1,3,3-tetramethyldisiloxane may be 0.1 to 100 hours, preferably 1 to 50 hours. Within less than 0.1 hour, the amount of reaction heat per unit time would be large whereby the reaction system undergoes a rapid rise of temperature, causing hazards. A reaction time of more than 100 hours is economically disadvantageous.

Illustrative examples of 1-(alkoxysilyl)ethyl-1,1,3,3-tetramethyldisiloxanes having the general formula (2):

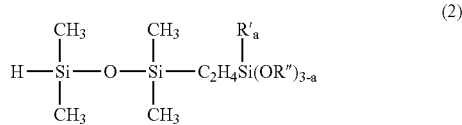

wherein R', R" and a are as defined above are given below although the invention is not limited thereto. It is understood that the structural formula shown below implicates a mixture of two isomers (i.e., alpha- and beta-adducts) while the two isomers have the structures according to the general formulae (4) and (5) and their ratio (isomeric ratio) is as specified above.

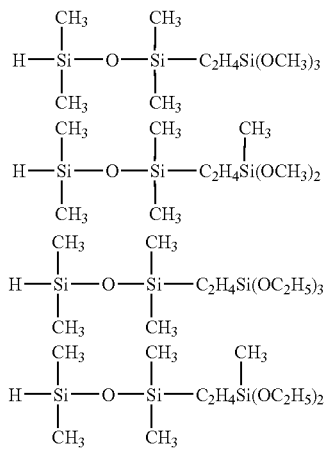

The 1-(alkoxysilyl)ethyl-1,1,3,3-tetramethyldisiloxane product obtained by the inventive method may be purified to a high purity by ordinary distillation under a reduced pressure of up to 13 kPa, especially up to 7 kPa.

EXAMPLE

The following Examples are included for illustrative purposes only and should not be construed as limiting the invention.

Example 1

A four-necked flask equipped with a reflux condenser, stirrer, addition funnel and thermometer was thoroughly purged with nitrogen. In the nitrogen blanket, the flask was charged with 134.3 g (1 mol) of 1,1,3,3-tetramethyldisiloxane and 0.026 g (0.1 mmol) of $RhCl_3 \cdot 3H_2O$ to form a mixture. The mixture was heated to 60-70° C. and maintained at the temperature. With stirring, 148.2 g (1 mol, equimolar to 1,1,3,3-tetramethyldisiloxane) of vinyltrimethoxysilane was added dropwise to the mixture from the addition funnel over 6 to 7 hours. After the completion of dropwise addition, the reaction mixture was maintained at 60-70° C. and aged for 1 to 2 hours, driving the reaction to completion. On vacuum distillation, a product having a boiling point of 92-95° C. at 1.3 kPa was collected. The 1-(trimethoxysilyl)ethyl-1,1,3,3-tetramethyldisiloxane product was obtained in a yield of 93%. On gas chromatography analysis, the product was identified to be a mixture of two isomers, alpha-adduct:
1-[1-(trimethoxysilyl)ethyl]-1,1,3,3-tetramethyldisiloxane and beta-adduct: 1-[2-(trimethoxysilyl)ethyl]-1,1,3,3-tetramethyldisiloxane. The isomeric ratio of alpha-adduct/beta-adduct was 18/82.

Example 2

Reaction was effected as in Example 1 except that 0.025 g (0.05 mmol) of $[RhCl(cod)]_2$ wherein "cod" stands for 1,5-cyclooctadiene was used in place of 0.026 g of $RhCl_3 \cdot 3H_2O$. The product was obtained in a yield of 90%. The isomeric ratio of alpha-/beta-adduct was 18/82.

Example 3

Reaction was effected as in Example 1 except that 0.093 g (0.1 mmol) of $RhCl(PPh_3)_3$ was used in place of 0.026 g of $RhCl_3 \cdot 3H_2O$. The product was obtained in a yield of 90%. The isomeric ratio of alpha-/beta-adduct was 18/82.

Comparative Example 1

Reaction was effected as in Example 1 except that 2.0 g (containing 0.1 mmol of Pt) of a known Karstedt platinum catalyst (Pt 1 wt %) was used in place of 0.026 g of $RhCl_3 \cdot 3H_2O$. Vinyltrimethoxysilane was added dropwise over 11 hours. The reaction mixture was aged for 2 hours, driving the reaction to completion. The product was obtained in a yield of 64%. The isomeric ratio of alpha-/beta-adduct was 30/70.

Comparative Example 2

Reaction was effected as in Example 1 except that 2.0 g (containing 0.1 mmol of Pt) of a known Speier platinum catalyst (Pt 1 wt %) was used in place of 0.026 g of $RhCl_3 \cdot 3H_2O$. Vinyltrimethoxysilane was added dropwise over 10 hours. The reaction mixture was aged for 3 hours, driving the reaction to completion. The product was obtained in a yield of 64%. The isomeric ratio of alpha-/beta-adduct was 30/70.

Comparative Example 3

Reaction was effected as in Comparative Example 1 except that the amount of 1,1,3,3-tetramethyldisiloxane was increased from 134.3 g (1 mol) to 179.0 g (1.333 mol).

Vinyltrimethoxysilane was added dropwise over 17 hours. The reaction mixture was aged for 2 hours, driving the reaction to completion. The product was obtained in a yield of 72% (relative to the vinyltrimethoxysilane) and 54% (relative to the 1,1,3,3-tetramethyldisiloxane). The isomeric ratio of alpha-/beta-adduct was 28/72.

Comparative Example 4

Reaction was effected as in Example 1 except that 0.079 g (0.1 mmol) of cis-PtCl$_2$(PPh$_3$)$_2$ was used as the catalyst in place of 0.026 g of RhCl$_3$·3H$_2$O. It was confirmed that at the time when about 100 g of vinyltrimethoxysilane had been added dropwise, a large amount of the unreacted vinyltrimethoxysilane accumulated in the reaction mixture so that the reaction had been deactivated. The process was interrupted at this point.

Comparative Examples 1-4 demonstrate that when platinum compounds are used as the reaction catalyst, the same reaction process results in very low yields and more amounts of alpha-adduct.

Example 4

Reaction was effected as in Example 1 except that the reaction temperature was 40-50° C. The product was obtained in a yield of 94%. The isomeric ratio of alpha-/beta-adduct was 15/85.

Example 5

Reaction was effected as in Example 4 except that 0.025 g (0.05 mmol) of [RhCl(cod)]$_2$ was used in place of 0.026 g of RhCl$_3$·3H$_2$O. The product was obtained in a yield of 95%. The isomeric ratio of alpha-/beta-adduct was 15/85.

Reference Example 1

Reaction was effected as in Example 4 except that 0.093 g (0.1 mmol) of RhCl(PPh$_3$)$_3$ was used in place of 0.026 g of RhCl$_3$·3H$_2$O. It was confirmed that at the time when about 70 g of vinyltrimethoxysilane had been added dropwise, a large amount of the unreacted vinyltrimethoxysilane accumulated in the reaction mixture so that the reaction had been deactivated. The process was interrupted at this point.

This demonstrates that in order for stable addition reaction to proceed to completion at a reaction temperature of less than 60° C., rhodium compounds which do not contain as the ligand a phosphorus-containing compound which can interfere with addition reaction between H—Si groups and vinyl groups are preferred, with rhodium compounds containing rhodium halide or 1,5-cyclooctadiene as the ligand being especially preferred.

Comparative Example 5

A four-necked flask equipped with a reflux condenser, stirrer, and addition funnel was thoroughly purged with nitrogen. In the nitrogen blanket, the flask was charged with 0.5 mg (0.002 mmol) of RhCl$_3$·3H$_2$O. The reactor was heated to 40-50° C. and maintained at the temperature. With stirring, a mixture of 2.7 g (0.02 mol) of 1,1,3,3-tetramethyldisiloxane and 3.0 g (0.02 mol, equimolar to 1,1,3,3-tetramethyldisiloxane) of vinyltrimethoxysilane was dumped all at once from the addition funnel. The mixture of these three components was allowed to react. The reaction mixture was aged for about 12 hours. The product was obtained in a yield of 61%. The isomeric ratio of alpha-/beta-adduct was 30/70.

Comparative Example 6

Reaction was effected as in Comparative Example 5 except that 1.9 mg (0.002 mmol) of RhCl(PPh$_3$)$_3$ was used in place of 0.5 mg of RhCl$_3$·3H$_2$O. After 4 hours of aging, the product was obtained in a yield of 75%. The isomeric ratio of alpha-/beta-adduct was 26/74.

Comparative Examples 5-6 demonstrate that if 1,1,3,3-tetramethyldisiloxane and vinyl-containing alkoxysilane are reacted all at once, even in the presence of a rhodium compound, undesired results are obtained including reduced percent yields due to a phenomenon that reactivity lowers or more by-products form and an increased isomeric ratio of alpha-adduct/beta-adduct (more alpha-adduct formation).

Japanese Patent Application No. 2005-235246 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A method for preparing a 1-(alkoxysilyl)ethyl-1,1,3,3-tetramethyldisiloxane having the general formula (2):

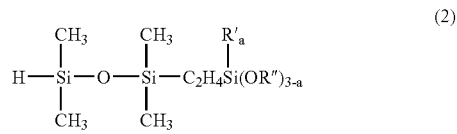

wherein R' and R" are methyl or ethyl and may be the same or different, and a is equal to 0, 1 or 2,
said method comprising adding dropwise a vinyl-containing alkoxysilane having the general formula (1):

wherein R' and R" are methyl or ethyl and may be the same or different, and a is equal to 0, 1 or 2, to 1,1,3,3-tetramethyldisiloxane in the presence of a rhodium compound, and effecting reaction.

2. The method of claim 1 wherein the reaction is at a temperature in the range from 0° C. to less than 60° C.

3. The method of claim 1 wherein the rhodium compound is free of a phosphorus-containing compound as a ligand.

4. The method of claim 1 wherein the rhodium compound contains rhodium halide or 1,5-cyclooctadiene as a ligand.

5. The method of claim 1 wherein the vinyl-containing alkoxysilane is vinyltrimethoxysilane, and the product 1-(alkoxysilyl)ethyl-1,1,3,3-tetramethyldisiloxane is 1-(trimethoxysilyl)ethyl-1,1,3,3-tetramethyldisiloxane.

6. The method of claim 1 wherein in general formula (1) R' is methyl, R" is methyl or ethyl and a is 0 or 1.

7. The method of claim 1 wherein the vinyl-containing alkoxysilane is at least one selected from the group consisting of

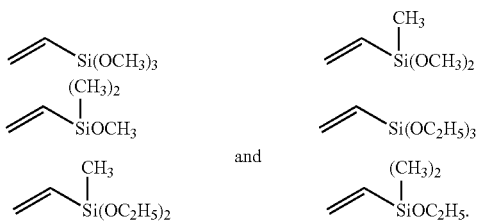
and

8. The method of claim 1 wherein the molar ratio of the vinyl-containing alkoxysilane to 1,1,3,3-tetramethyldisiloxane is in a range of from 0.8 to 1.2.

9. The method of claim 1 wherein the molar ratio of the vinyl-containing alkoxysilane to 1,1,3,3-tetramethyldisiloxane is in a range of from 0.9 to 1.1.

10. The method of claim 1 wherein said rhodium compound is at least one selected from the group consisting of $RhCl_3 \cdot xH_2O$, $RhCl_3$, $RhBr_3 \cdot 2H_2O$, $RhBr_3$, $RhI_3$, $Rh_6(CO)_{16}$, $Rh_4(CO)_{12}$, $[RhCl(CO)_2]_2$, $Rh(acac)_3$, $[Rh(acac)_2]_2$, $Rh(acac)(CO)_2$, $(NH_4)_3[RhCl_6] \cdot xH_2O$, $[Rh(NH_3)_5Cl]Cl_2$, $[Rh(C_7H_{15}COO)_2]_2$, $[Rh(CF_3COO)_2]_2$, $[Rh(C_2H_4)_2(acac)]$, $[Rh(C_2H_4)_2]_2$, $[RhCl(C_8H_{14})_2]_2$, $[RhCl(C_7H_8)]_2$, $(CH_3)_5C_5Rh(CO)_2$, $[(CH_3)_5C_5RhCl_2]_2$, $Rh(C_2H_8N_2)_3Cl_3 \cdot 3H_2O$, $[RhCl(cod)]_2$, $[RhOH(cod)]_2$, $[Rh(cod)_2(acac)]$, $[Rh(cod)(acac)]$, $Rh(cod)_2BF_4$, $Rh(cod)_2SO_3CF_3$, $RhCl(PPh_3)_3$, $[Rh(acac)(CO)(PPh_3)_3]$ and trans-$[RhH(CO)(PPh_3)_3]$, where "acac" designates acetylacetonato, "cod" designates $_{1,5}$-cyclooctadiene, and "PPh_3" designates triphenylphosphine.

11. The method of claim 1 wherein said rhodium compound is used in an amount of from $0.1 \times 10^{-6}$ to 0.1 mole of Rh atom per mole of 1,1,3,3-tetramethyldisiloxane.

12. The method of claim 1 wherein said rhodium compound is used in an amount of from $1 \times 10^{-6}$ to 0.01 mole of Rh atom per mole of 1,1,3,3-tetramethyldisiloxane.

13. The method of claim 1 wherein the rhodium compound is premixed with the 1,1,3,3-tetramethyldisiloxane prior to the addition of the vinyl-containing alkoxysilane.

14. The method of claim 1 wherein the 1-(alkoxysilyl)ethyl-1,1,3,3-tetramethyldisiloxane includes an alpha-adduct isomer of general formula (4) and a beta-adduct isomer of general formula (5):

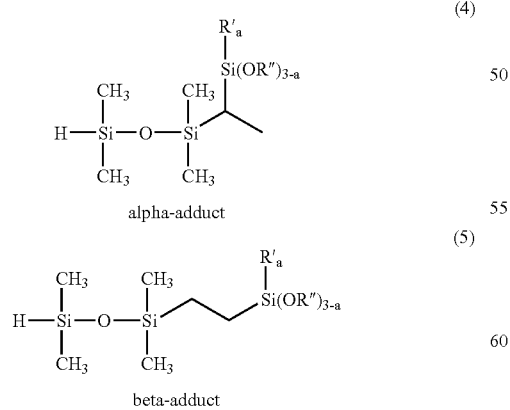

wherein R' and R" are methyl or ethyl and may be the same or different, and a is equal to 0, 1 or 2.

15. The method of claim 14 wherein the isomeric ratio of alpha-adduct/beta-adduct is (25 or less)/(75 or more).

16. The method of claim 1 wherein the 1-(alkoxysilyl)ethyl-1,1,3,3-tetramethyldisiloxane is selected from the group consisting of

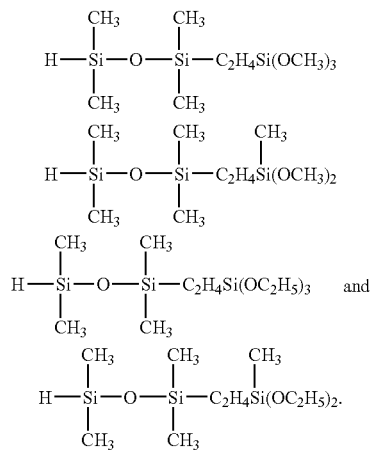

17. The method of claim 1 further comprising purifying by distillation under a reduced pressure of up to 13 kPa.

18. The method of claim 1 wherein the reaction is at a temperature in the range from 0° C. to 150° C.

19. A method for preparing a 1-(alkoxysilyl)ethyl-1,1,3,3-tetramethyldisiloxane having the general formula (2):

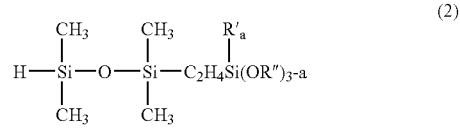

wherein R' and R" are methyl or ethyl and may be the same or different, and a is equal to 0, 1 or 2, said method comprising adding dropwise a vinyl-containing alkoxysilane having the general formula (1):

wherein R' and R" are methyl or ethyl and may be the same or different, and a is equal to 0, 1 or 2, to 1,1,3,3-tetramethyldisiloxane in the presence of a rhodium compound, and effecting reaction at a temperature in the range from 0° C. to less than 60° C., wherein the rhodium compound is free of a phosphorus-containing compound as a ligand.

* * * * *